United States Patent
Van Zon et al.

(10) Patent No.: US 8,933,694 B2
(45) Date of Patent: Jan. 13, 2015

(54) MIXED ACTUATION PROTOCOL FOR A MAGNETIC BIOSENSOR DEVICE

(75) Inventors: Hans Van Zon, Waalre (NL); Mykhaylo Ovsyanko, Eindhoven (NL)

(73) Assignee: Koninklijkle Philips N.V., Eindhoven (NL)

( * ) Notice: Subject to any disclaimer, the term of this patent is extended or adjusted under 35 U.S.C. 154(b) by 699 days.

(21) Appl. No.: 13/145,463

(22) PCT Filed: Apr. 9, 2009

(86) PCT No.: PCT/IB2009/051496
§ 371 (c)(1),
(2), (4) Date: Jul. 20, 2011

(87) PCT Pub. No.: WO2010/084383
PCT Pub. Date: Jul. 29, 2010

(65) Prior Publication Data
US 2011/0279114 A1    Nov. 17, 2011

(30) Foreign Application Priority Data

Jan. 22, 2009  (EP) .................................... 09151058

(51) Int. Cl.
| | |
|---|---|
| *G01R 33/02* | (2006.01) |
| *G01N 27/74* | (2006.01) |
| *G01R 33/12* | (2006.01) |
| *G01N 33/543* | (2006.01) |
| G01N 21/55 | (2014.01) |
| G01N 35/00 | (2006.01) |

(52) U.S. Cl.
CPC .......... *G01R 33/1269* (2013.01); *G01N 27/745* (2013.01); *G01N 33/54333* (2013.01); *G01N 21/552* (2013.01); *G01N 35/0098* (2013.01)
USPC ........................ 324/244; 324/244.1; 324/204

(58) Field of Classification Search
USPC ....................................... 324/244, 244.1, 204
See application file for complete search history.

(56) References Cited

FOREIGN PATENT DOCUMENTS

| | | |
|---|---|---|
| EP | 1469311 A1 | 10/2004 |
| JP | 2007271573 A | 10/2007 |
| WO | 2005111615 A1 | 11/2005 |
| WO | 2006035359 A2 | 4/2006 |
| WO | 2008044214 A | 4/2008 |
| WO | 2008102218 A1 | 8/2008 |
| WO | 2008107827 A1 | 9/2008 |

*Primary Examiner* — Reena Aurora

(57) ABSTRACT

The present invention provides a magnetic biosensor device comprising a sensor cartridge for receiving an assay to be tested, an electromagnetic unit for producing a magnetic field at a sensor surface of the sensor cartridge, and detection means for detecting the presence of magnetic particles close to the sensor surface. The electromagnetic unit is adapted to periodically produce a magnetic field having at least a first and a second magnetic field strength, the ratio of the amount of time of applying the first magnetic field strength to the amount of time of the period of applying the first and the second field strength being varied during the measurement. The invention further provides a method for applying a magnetic field to a sensor surface of a magnetic bio sensor device.

14 Claims, 4 Drawing Sheets

MIXED ACTUATION PROTOCOL FOR A MAGNETIC BIOSENSOR DEVICE

FIELD OF THE INVENTION

The invention relates to magnetic biosensor devices, in particular to actuation of magnetic particles toward a sensor surface of the biosensor device.

BACKGROUND OF THE INVENTION

The demand for biosensors is increasingly growing these days. Usually, biosensors allow for the detection of a given specific molecule within an analyte, wherein the amount or concentration of said target molecule is typically small. For example, the amount of drugs or cardiac markers within saliva or blood may be measured. Drugs-of-abuse are generally small molecules that only possess one epitope and for this reason cannot be detected, e.g., by a sandwich assay. A competitive or inhibition assay is a preferred method to detect these molecules. A well-known competitive assay setup is to couple the target molecules of interest onto a surface, and link antibodies to a label or detection tag, that may be an enzyme, a fluorophore or magnetic beads. This system is used to perform a competitive assay between the target molecules from the sample and the target molecules on the surface, using the tagged antibodies. For road-side testing, the assay should be fast and robust.

In a magnetic-label biosensor, measuring the presence of certain biochemical agents such as drugs or cardiac markers is based on molecular capture and labeling with magnetic particles or beads. Magnetic attraction of the beads, also referred to as actuation, is essential in order to increase the performance, i.e. speed, of the biosensor for point-of-care applications. The direction of the magnetic attraction can be either towards the surface where the actual measurement is carried out or away from this surface. In the first case magnetic actuation allows the enhancement of concentration of magnetic particles near the sensor surface, speeding up the binding process of the magnetic particles at the sensitive surface. In the second case particles are removed from the surface which is called magnetic washing. Magnetic washing can replace the traditional wet washing step. It is more accurate and reduces the number of operating actions.

In a typical set-up of a magnetic biosensor device such as a biosensor device based on Frustrated Total Internal Reflection (FTIR), the magnetic beads are arranged in a sensor chamber of a sensor cartridge. At least a portion of a sensor surface in the sensor chamber is prepared for the detection of the target molecules. For performing the test, the cartridge is placed in a reader comprising magnetic units for generating a magnetic field at the sensor surface, and detection means for detecting the presence of magnetic beads near the sensor surface. To increase the reaction speed of the target molecules in a liquid which is inserted into the cartridge, the magnetic units arranged below the cartridge generate a magnetic field to pull the beads towards the sensor surface when cartridge is placed in the reader.

Due to magnetic attraction, the number of magnetic beads near the sensor surface of the biosensor device increases and the sensor signal increases in time. To attract the particles to the surface, a so-called pulsed magnetic attraction schedule may be used. In such a scheme, the magnetic field is periodically switched on and off as described for example in WO 2008/102218 A1. When the magnetic field is on, beads are attracted towards a region close to the surface. When the magnetic field is switched off, beads will diffuse towards the surface or away from the surface, depending of their original position. It is generally observed during measurements that during such a pulsed attraction scheme the signal near the center of the attraction magnet increases more rapidly than the signal near one of the poletips of the magnet.

This effect slows down the overall speed of the assay because the speed is dominated by the positions near the poletips. In practice, this problem can be circumvented by only using a few positions or Regions-Of-Interest near the center of the magnet. This is not a limitation in the case that only one type of target molecules has to be measured. However, for multi-analyte assays or multi-chamber configurations this is a limitation.

SUMMARY OF THE INVENTION

There is a need to increase the overall speed and/or uniformity of the optical signal in a magnetic biosensor device. In particular, multi-analyte assays or multi-chamber configurations should become possible while still using the current hardware configuration.

According to the present invention, a magnetic biosensor device comprising a sensor cartridge for receiving an assay to be tested, an electromagnetic unit for producing a magnetic field at a sensor surface of the sensor cartridge, and detection means for detecting the presence of magnetic particles close to the sensor surface is provided. The electromagnetic unit is adapted to produce a magnetic field having at least a first and a second magnetic field strength to be applied to attract the beads to the sensor surface. The ratio of the amount of time of applying the first magnetic field strength to the amount of time of the complete period of applying the first and the second field strength is varied during the measurement. In the case where the second magnetic field strength is zero while the first magnetic field strength amounts to a predetermined field strength attracting the beads to the sensor surface, this ratio is called duty-cycle. Thus, the duty-cycle is varied in a defined way during the measurement.

In a preferred embodiment of the present invention, the ratio of the amount of time of applying the first magnetic field strength to the amount of time of the period of applying the first and the second field strength decreases during the measurement. The variation of the ratio during the measurement may be performed in a continuous manner or in a stepwise manner, having at least one predetermined ratio at the beginning of the measurement and another predetermined ratio at the end of the measurement.

Preferably, the ratio at the beginning of the measurement is larger than 50%, preferably 85%, while the ratio at the end of the measurement is less than 50%, preferably about 15%.

In one embodiment of the present invention, the detection means comprised in the magnetic biosensor device comprises a light source for directing light onto the sensor surface at an angle of total internal reflection and a detector for detecting light reflected from the sensor surface. That is, the magnetic biosensor device is based on a measurement of frustrated total internal reflection.

Another example of the invention describes a first electromagnetic unit which generates the first magnetic field strength essentially perpendicular to the sensor surface and a second electromagnetic unit which generates the second magnetic field strength essentially parallel to the sensor surface, the first and second electromagnetic units are adapted to alternately produce the first magnetic field strength and the second magnetic field strength, respectively, with a period of time between the generation of the first magnetic field strength and the second magnetic field strength in which no magnetic field is generated. This configuration provides a magnetic field strength essentially parallel to the sensor surface by the second electromagnetic unit and a magnetic field strength essentially perpendicular to the sensor surface by the first electromagnetic unit successively. It was found advantageous when both electromagnetic units are down for a time between the times when first and second electromagnetic unit are on to produce a corresponding magnetic field. The time sequence is thus described in three steps, one first step is a field pulse parallel to the sensor surface, a second step is a field pulse perpendicular to the surface, and a third step is a time duration smaller than the other pulse durations without a magnetic field applied. By the three step method and corresponding device described a randomizing and mixing effect of the magnetic particles is achieved, which are regularly dissolved in a fluid.

Furthermore, the present invention provides a method for attracting magnetic beads in a magnetic biosensor device.

These and other aspects of the invention will be apparent from and elucidated with reference to the embodiments described hereafter.

DETAILED DESCRIPTION OF EMBODIMENTS

The reason why in a magnetic biosensor device a pulsed actuation protocol works better than a continuous magnetic actuation protocol under the condition that both methods consume the same amount of energy can be explained as follows.

On first thought one would expect that continuous magnetic attraction is better than pulsed actuation because during a larger amount of time the magnetic beads are attracted towards the surface. This is only partially true. Indeed more magnetic particles 10, also referred to as beads or particles in the following, are collected near the sensor surface 2 in the same amount of time by continuous attraction. However, from experiments it has been shown that only a small fraction of the particles 10 which are collected near the surface will actually be able to reach and bind to the surface. This is caused by the magnetic bead-bead interaction, as illustrated in FIG. 1.

Figure 1:
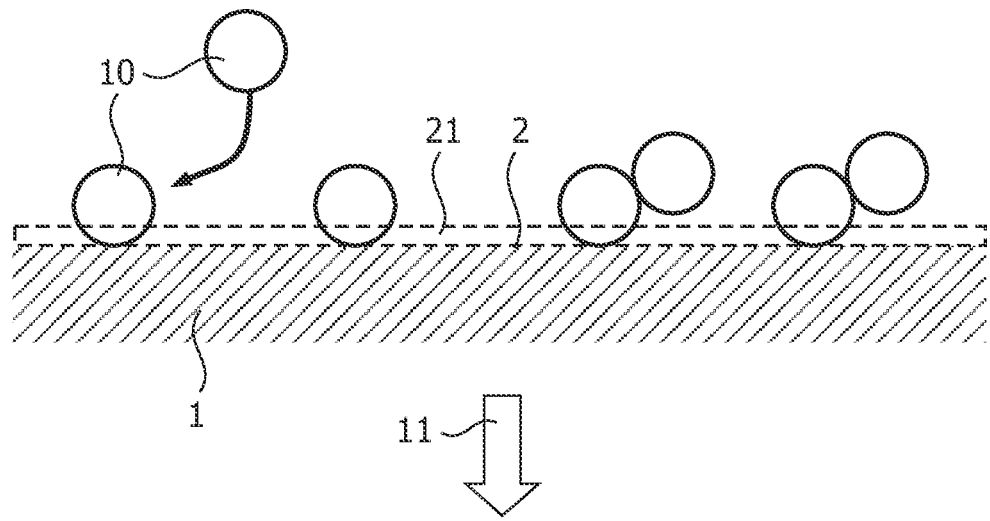
FIG. 1 illustrates the process of clustering of magnetic beads during continuous attraction to a sensor surface, FIG. 2 schematically shows the direction of magnetic field lines typically produced at the sensor surface of a magnetic biosensor device.

In FIG. 1 the lower wall 1 of a sensor chamber in a sensor cartridge 1 for a magnetic biosensor is schematically shown. The term magnetic biosensor is defined here as a sensor containing a biological assay in which magnetic particles 10 take part in the process of binding of analytes to be detected to the biological assay, which is well known in the art. The wall 1 forms a sensor surface 2 of the sensor chamber. Below the sensor surface 2, an electromagnetic unit is arranged, which typically is formed by two pole tips arranged close to the edges of the sensor surface (see also poletips 3 shown in FIG. 2). When applying a magnetic force as illustrated by arrow 11 the beads 10 are attracted towards the sensor surface 2. As soon as the surface 2 is covered with a certain amount of beads 10, e.g. approximately 10% at the center but even lower near the poletips 3 close to the edge of the sensor surface 2, beads 10 approaching the surface 2 will be attracted by the beads 10 which are already present on the surface 2 due to the magnetic actuation force. This process is known as 'clustering'. Because the magnetic field makes an angle with the surface, the clustered beads 10 will be outside a detection region 21 of the sensor surface 2, i.e. the evanescent field in case of a FTIR biosensor.

Thus, although these beads 10 are attracted by the magnetic field, they will not make contact with the surface 2 and therefore cannot bind to the surface 2. Only when the magnetic field is switched off, the clustered beads 10 will be released and by diffusion are able to make contact with the surface 2. When the magnetic field is continuously switched on, the clustered beads 10 will never come into contact with the surface and the signal remains low, typically only 3-10% of the available 100% signal. Therefore, for a pulsed actuation protocol both the attraction time $t_{ON}$ as well as the time that the magnetic field is switched off $t_{OFF}$ are important.

During the attraction time the beads are transported to a region near the surface where the concentration of beads increases. During the time the magnetic field is off, the beads can actually reach the surface through diffusion and bind. The ratio $t_{ON}/(t_{ON}+t_{OFF})$ is called the "duty-cycle" (DC) of the actuation protocol. To achieve quickly a large signal, the number of beads transported to a region near the surface during the ON-phase should match the number of beads transported to the surface by means of diffusion during the OFF-phase. This can be equated as follows:

$$R_{ON} \cdot t_{ON} = R_{OFF} \cdot t_{OFF} \qquad (1)$$

where $R_{ON}$ and $R_{OFF}$ are respectively the transport rates, expressed in beads/sec, during the ON and OFF phase, i.e. the transport rates during magnetic attraction and diffusion. The optimum duty-cycle of the pulsed signal can therefore be expressed in the transport rates:

$$\frac{R_{OFF}}{R_{ON} + R_{OFF}} = DC \qquad (2)$$

This equation shows that the duty-cycle of the pulsed actuation signal is important and has to be optimized given the transport rates of the system.

Figure 2:
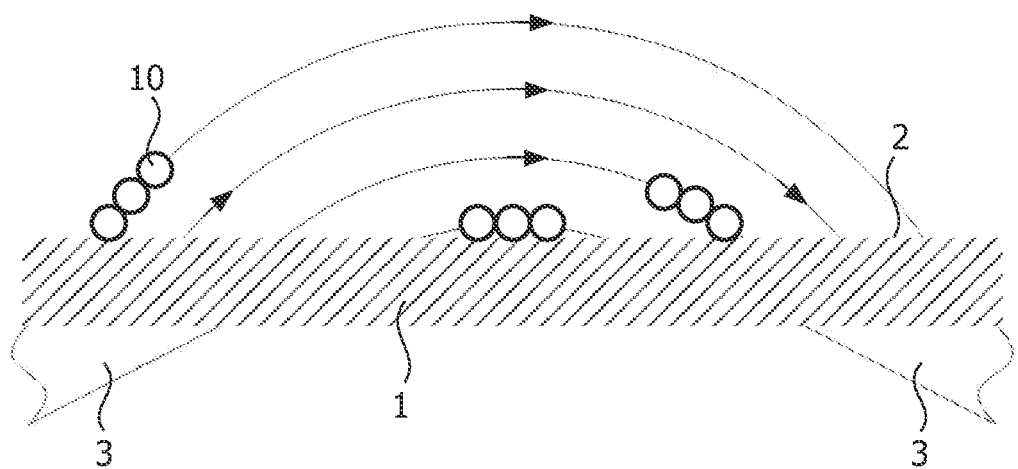

As illustrated in FIG. 2, the magnetic field of the attraction magnet intersects the surface 2 under a certain angle. This angle is zero exactly between the poletips 3 of an ideal magnet and can become several tens of degrees, e.g. 30 degrees, near the poletips 3. Therefore, at the center the direction of the magnetic field is parallel to the surface 2 while near the poletips 3 it is pointing more upwards or downwards. The direction of the magnetic field determines the direction in which the clusters of beads 10 are formed. When the clusters have been formed under magnetic actuation and subsequently the field is switched off, the beads have to diffuse towards the surface 2. The larger the angle of the cluster, the more time it takes for the beads 10 to diffuse. The transport rate through diffusion near the poletips 3 will therefore be smaller than at the center of the magnet. From Equation 2 it can be seen that when the transport rate $R_{OFF}$ becomes smaller, a smaller duty-cycle for the pulsed actuation has to be chosen, expressing that more time is required for the diffusion step.

Figure 3:
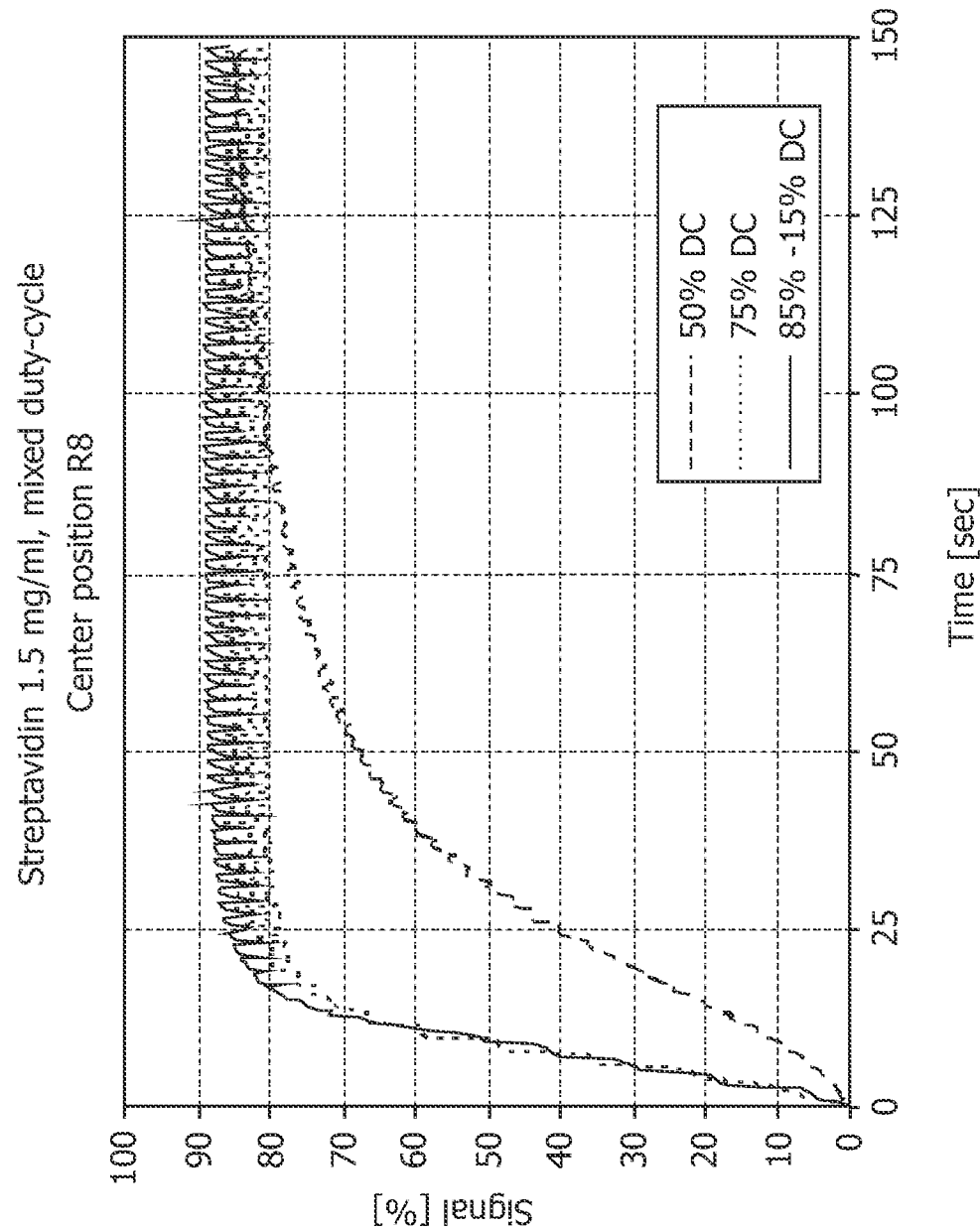
FIG. 3 shows the optical signals recorded at the center of the magnetic unit in a magnetic biosensor device using different actuation protocols.

In FIG. 3 recorded optical signals at the center position, i.e. in the center between the poletips of the magnetic unit, are shown for three different actuation protocols. Because the diffusion speed is high at the center of the sensor surface between the poletips (the beads only have to travel a short distance to the surface), increasing the duty-cycle and thus increasing the collection speed of the beads to a region near the surface increases the signal rate.

According to the first protocol (dashed curve) the duty-cycle of the applied pulsed magnetic field is 50% during the whole measurement, in the second protocol (dotted curve) the duty-cycle is 75% during the whole measurement, and in the third protocol (continuous curve), a combination of duty-cycles is applied, the duty-cycle being 85% at the beginning of the measurement and 15% at the end of the measurement. It is clearly visible that a 50% duty-cycle gives a slower signal than the 75% duty-cycle in this case.

Figure 4:
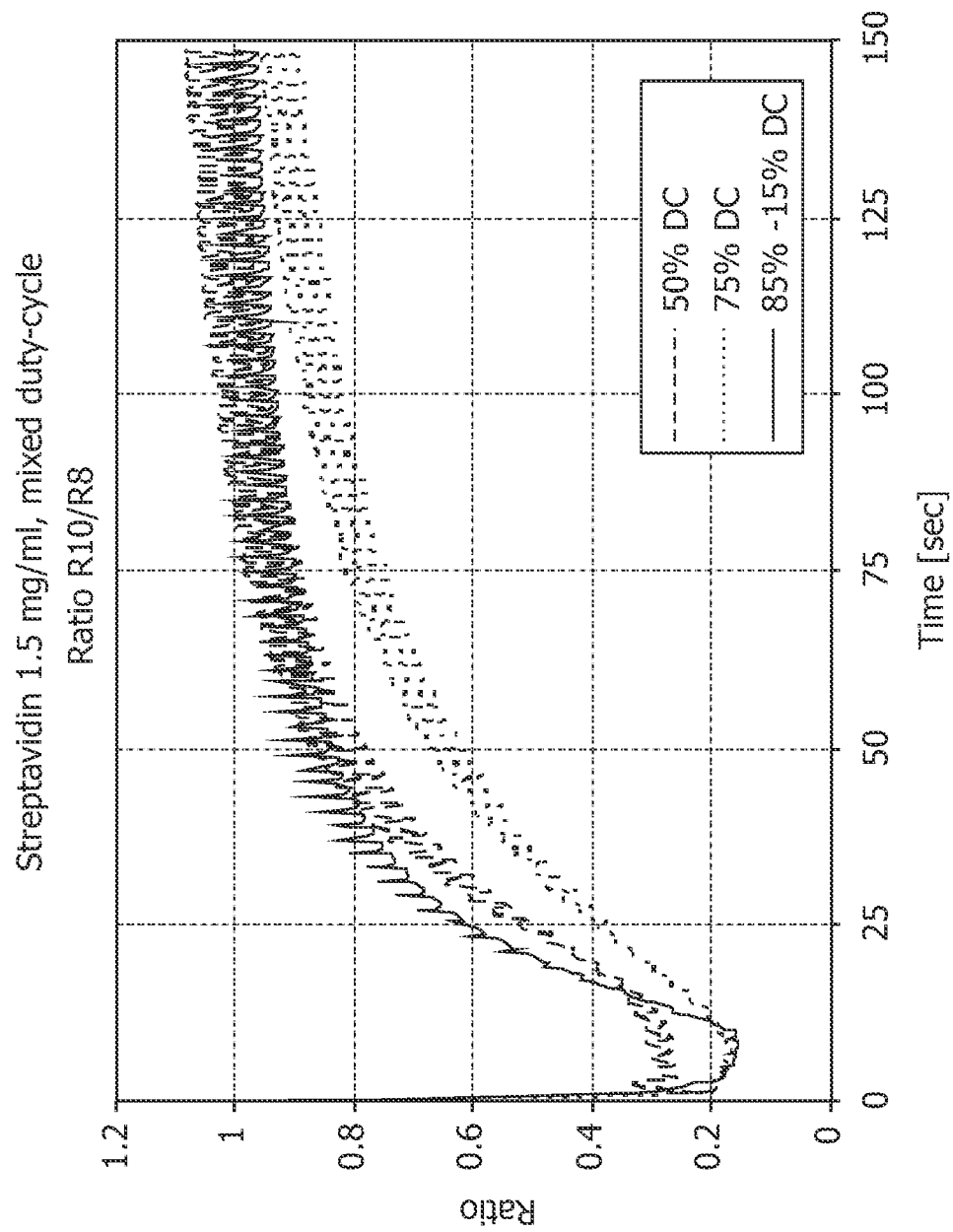
FIG. 4 shows the ratio of the signals recorded at the center and at the poletips of the magnetic unit in a magnetic biosensor device using different actuation protocols.

In FIG. 4 the ratio between the signal near the poletip and the signal at the center of the surface is plotted. A ratio of 1 indicates that the signal near the poletip is equal in strength to the signal at the center. This is the preferred situation and it is the goal of the actuation protocol to establish this ratio of 1 as close as possible and as fast as possible. A lower ratio indicates that the signal near the poletip lags behind the signal at the center. It is apparent that the ratio improves when more time for diffusion is given in the actuation protocol, i.e. when a lower duty-cycle is applied. The 50% duty-cycle gives a better ratio than the 75% duty-cycle. However, for the center position the opposite is true: 75% duty-cycle gives a faster signal than 50% duty-cycle.

A combination of duty-cycles as shown with the continuous curve, e.g. in a first step a duty-cycle of 85% to quickly collect beads near the surface and in a second step a larger diffusion time to improve the signal speed near the poletips, improves the ratio between poletip and center without compromising the signal at the center.

Accordingly, an actuation protocol consisting of two or more steps with different duty-cycles can improve the overall performance of the optical biosensor system. It enlarges the usable area on the surface between the magnet poles, improves the uniformity of signals between different measurement spots, and/or allows multi-analyte assays and/or multi-chamber configurations.

Due to differences in the magnetic field direction over the surface which may result from the hardware configuration of the magnet, the transport rates with which beads can be brought into contact with the surface are dependent on the position on the surface. An actuation protocol with a varying duty-cycle during the measurement, e.g. consisting of subsequent steps with different duty-cycles, can improve the overall speed and uniformity of the recorded signal.

Figure 5:
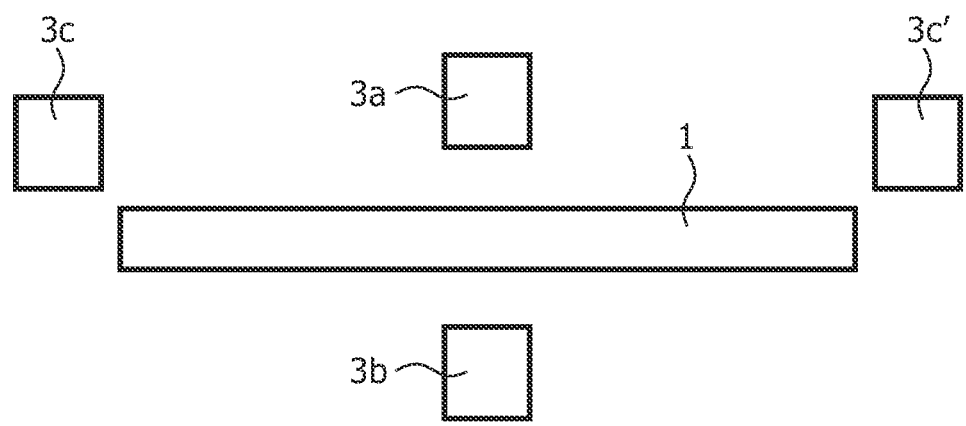
FIG. 5 shows a schematic view of an example of the invention with the sensor surface, one electromagnetic unit above the sensor surface, one electromagnetic unit below the sensor surface, and two electromagnetic units besides the sensor surface to enable a magnetic actuation with different force directions in relation to the sensor surface.

In the following a further example of the invention is described with regard to FIG. 5. FIG. 5 shows a schematic view of the sensor surface 1 described above as a part of a cartridge 1 of a biosensor device which uses magnetic particles 10, also called magnetic beads. In the configuration shown several electromagnetic units 3a, 3b, 3c, 3c' are implemented to generate a magnetic field pattern useful for randomizing and mixing the fluid applied to the sensor surface 2. In this example one electromagnetic unit 3a, e.g. a controlled coil, is arranged above the sensor surface 2, one electromagnetic unit 3b is arranged below the sensor surface 2, and two electromagnetic units 3c, 3c' are arranged besides the sensor surface 2, the electromagnetic unit 3c left to the sensor surface 2, and the electromagnetic unit 3c' right to the sensor surface 2. The configuration shown in FIG. 5 enables a magnetic actuation with different force directions in relation to the sensor surface 2. By way of electromagnetic field theory the electromagnetic units 3a, 3b attract or repel the magnetic particles 10 in the area above the sensor surface 2 depending on the direction of the magnetic field generated. An attraction in this connection occurs when magnetic field lines are directed from above to below the image plane as shown, i.e. in the direction of the sensor surface 2 to achieve a binding to the assay applied there. Correspondingly, a repulsion occurs when magnetic field lines are directed from below to above the image plane as shown. With other words a magnetic field essentially perpendicular to the sensor surface 2 is generated. In the latter case a magnetic force is exerted on the magnetic particles 10 away from the sensor surface 2 to remove the magnetic particles 10 from the sensor surface 2. Further configurations are designable, for instance with two electromagnetic units 3b below the sensor surface 2 on the cartridge 1 and one electromagnetic unit 3a above. Moreover, another electromagnetic unit 3c is arranged left to the cartridge 1 with sensor surface 2 and another electromagnetic unit 3c' is arranged right to the cartridge 1 with sensor surface 2. The electromagnetic units 3c, 3c' generate magnetic fields having magnetic field lines which are directed essentially parallel to the cartridge 1 with sensor and sensor surface 2 in any direction left or right to the image plane. The additional electromagnetic units 3c, 3c' besides the sensor surface 2 improve the binding behavior of the analyte to the assay at the sensor surface 2. When applying a magnetic field that is directed not only perpendicular but also parallel to the sensor surface 2 a randomizing and mixing of the magnetic particles 10 is achieved, which are commonly attached to the analyte to be detected by the biosensor. Controlling the four electromagnetic units 3a, 3b, 3c, 3c' was found to improve the process of binding the analyte to the assay, especially the number of specific bindings can be enhanced. This means, the detection of the effective amount of analyte in the fluid is improved as more analytes in the fluid are bound to the assay compared to a process with only magnetic fields perpendicular to the sensor surface 2. A further improvement of the process of specific binding is achieved by controlling the electromagnetic units 3a, 3b, 3c, 3c' in a way first applying a magnetic field pulse parallel to the sensor surface 2, then applying a magnetic field pulse perpendicular to the sensor surface 2, then applying no magnetic field within a short time period. The time periods of applied magnetic fields and the time period without a magnetic field are in the range of several seconds. The configuration described above is designed to efficiently transport magnetic particles 10 and the attached analyte from the fluid or bulk to the sensor surface 2.

Figure 6:
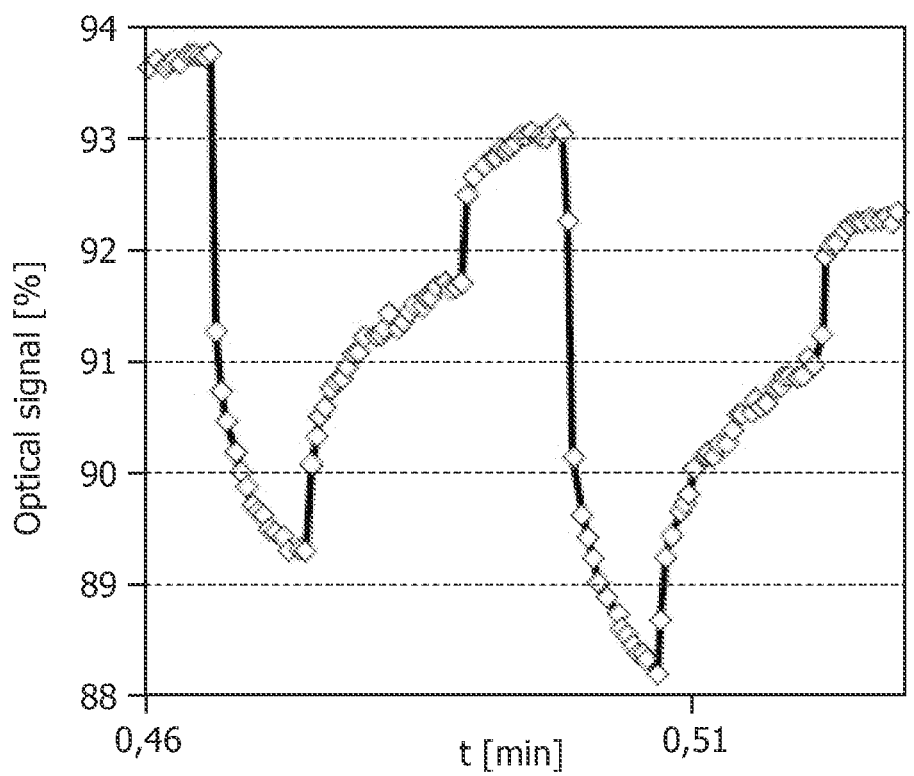
FIG. 6 shows a curve obtained by example of optical detection by the biosensor and the minimizing of aspecific bindings shown as a drop of the curve.

FIG. 6 shows a curve as a result of a measurement of the biosensor, by example done with an optical detection method, e.g. by frustrated total internal reflection (FTIR), with the configuration described under FIG. 5. The x-axis is designated as time in minutes, the y-axis is designated as a percentage of an optical signal detected by the biosensor. As visible in FIG. 6, the signal first has a nearly constant high level, then the randomizing and mixing is applied as described by actuating the electromagnetic units 3a, 3b, 3c, 3c'. The optical signal degrades and reaches a nearly constant level again which is lower than the original signal level. This lower constant signal level is explained as a reduction of aspecific bindings in the fluid, the specific bindings in relation to the aspecific bindings have increased. As shown, for some seconds the magnetic field is off, leading to the measured optical signal rising from a minimum to the nearly constant level, a kind of diffuse relaxation. Operating the process described under FIG. 5 the actuated magnetic field leads to another signal drop until a minimum of the signal is reached. Again, a time period when no magnetic field is generated leads to an increase of the signal up to an almost constant level which is again lower than the signal level measured before. Again, the part of the signal caused by aspecific binding is reduced. Applying the process repeatedly means to minimize the signal part caused by aspecific binding and enhancing of the correct signal caused by specific bindings.

While the invention has been illustrated and described in detail in the drawings and foregoing description, such illustration and description are to be considered illustrative or exemplary and non-restrictive; the invention is thus not limited to the disclosed embodiments. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. Any reference signs in the claims should not be considered as limiting the scope.

The invention claimed is:

1. A magnetic biosensor device comprising:
   (a) a sensor cartridge configured to receive an assay to be tested,
   (b) at least an electromagnetic unit configured to produce a magnetic field at a sensor surface of the sensor cartridge, and
   (c) means for detecting the presence of magnetic particles close to the sensor surface, wherein the electromagnetic unit is adapted to periodically produce a magnetic field having at least a first and a second magnetic field strength, a ratio of an amount of time of applying the first magnetic field strength to an amount of time of the period of applying the first and the second field strength being varied during the measurement.

2. The device according to claim 1, wherein the second magnetic field strength is zero.

3. The device according to claim 1, wherein the ratio decreases during the measurement.

4. The device according to claim 1, wherein the ratio varies continuously during the measurement.

5. The device according to claim 1, wherein the ratio varies in a stepwise manner during the measurement.

6. The device according to claim 1, wherein the ratio changes from about 85% to about 15% during the measurement.

7. The device according to claim 1, wherein the means for detecting the presence of magnetic particles close to the sensor surface comprises a light source for directing light onto the sensor surface at an angle of total internal reflection and a detector for detecting light reflected from the sensor surface.

8. The device according to claim 1, wherein a first electromagnetic unit generates the first magnetic field strength essentially perpendicular to the sensor surface and a second electromagnetic unit generates the second magnetic field strength essentially parallel to the sensor surface, the first electromagnetic unit and the second electromagnetic units are adapted to alternately produce the first magnetic field strength and the second magnetic field strength, respectively, with a period of time between the generation of the first magnetic field strength and the second magnetic field strength in which no magnetic field is generated.

9. A method for applying a magnetic field at a sensor surface of a magnetic biosensor device, the method comprising:
   periodically producing a magnetic field having at least a first and a second magnetic field strength, a ratio of an amount of time of applying the first magnetic field strength to an amount of time of the period of applying the first and the second magnetic field strength being varied during the measurement.

10. The method according to claim 9, wherein the second magnetic field strength is zero.

11. The method according to claim 9, wherein the ratio decreases during the measurement.

12. The method according to claim 9, wherein the ratio varies continuously during the measurement.

13. The method according to claim 9, wherein the ratio varies from about 85% to about 15% in a stepwise manner during the measurement.

14. The method according to claim 9, further comprising detecting a presence of magnetic particles close to a sensor surface by directing light onto the sensor surface at an angle of total internal reflection detecting light reflected from the sensor surface.

* * * * *